United States Patent [19]

Reiss et al.

[11] Patent Number: 5,000,191

[45] Date of Patent: Mar. 19, 1991

[54] FORCE-LIMITING ADAPTER FOR SURGICAL INSTRUMENTS

[76] Inventors: Serge Reiss, 13/2 Weizman Street, Nahariya, Israel; Joseph M. Brandes, 4 Kiryat Sefer Street, Haifa, Israel, 34676

[21] Appl. No.: 216,924

[22] Filed: Jul. 8, 1988

[30] Foreign Application Priority Data

Jul. 13, 1987 [IL] Israel .............................. 83174

[51] Int. Cl.⁵ .............................. A61B 10/00
[52] U.S. Cl. .............................. 128/757; 606/119; 606/160; 604/902
[58] Field of Search ............ 128/304, 303 R, 307, 128/311, 314, 315, 341, 357, 361, 749, 757, 758, 774, 778; 604/119, 902, 22; 606/119, 160

[56] References Cited

U.S. PATENT DOCUMENTS

| | | | |
|---|---|---|---|
| 55,620 | 6/1866 | Capewell | 128/314 |
| 3,394,699 | 7/1968 | Koett | 128/311 |
| 3,702,115 | 11/1972 | Elcaness | 128/276 |
| 4,178,810 | 12/1979 | Takahashi | 74/501 R |
| 4,462,405 | 7/1984 | Ehrlich | 128/329 R |
| 4,842,578 | 6/1989 | Johnson et al. | 604/22 |

*Primary Examiner*—C. Fred Rosenbaum
*Assistant Examiner*—Adam J. Cermak
*Attorney, Agent, or Firm*—Schweitzer, Cornman & Gross

[57] ABSTRACT

In combination with a surgical hand instrument applied by a pushing action to place the instrument against human tissue, followed by a pulling action along the tissue, the improvement consisting of an adapter apparatus to limit the pushing action of the instrument against the tissue to a predetermined force, the adapter being inoperative during the pulling action of the instrument. The adapter may advantageously include a biasing spring, which may be adjustable to set the level of the maximum force to be applied.

8 Claims, 4 Drawing Sheets

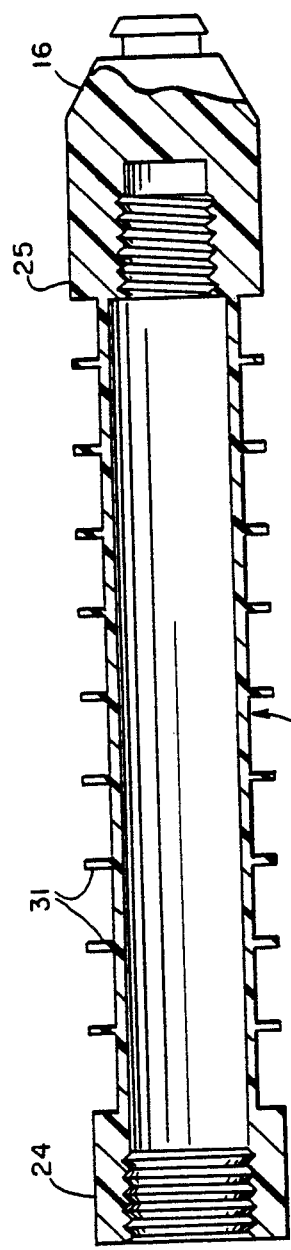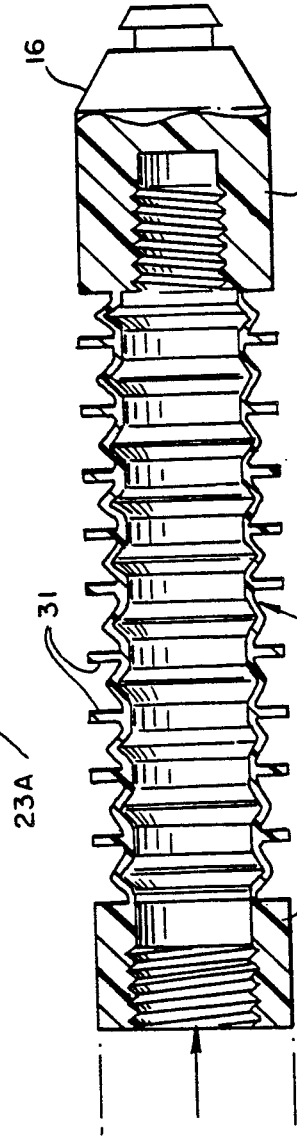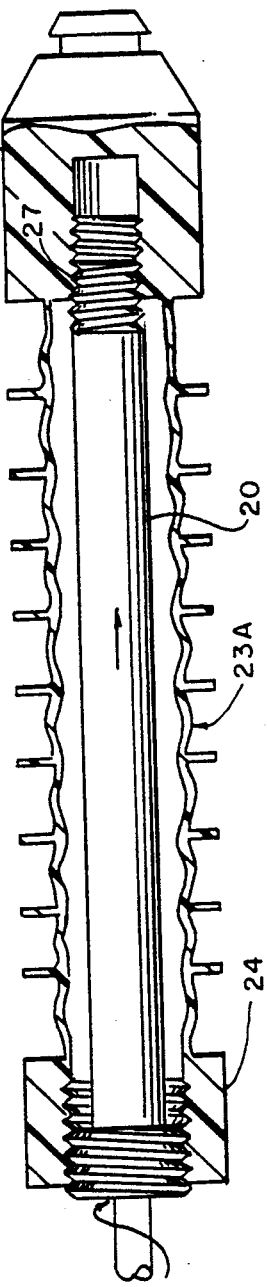

FORCE-LIMITING ADAPTER FOR SURGICAL INSTRUMENTS

This invention relates generally to surgical instruments, and more particularly, to improved gynecological instruments such as uterine probes and aspirating or vacuum curettes.

Common gynecological procedures, known as D &.C, (dilation and curettage) and D & E (dilation and evacuation), include the measurement of uterine length followed by curettage, commonly with aspiration. Both the sounding or measurement and the curettage procedures preliminarily involve the application of instruments against the uterine wall at the fundus portion of the womb cephalad from the line joining the entrances of the oviducts, Among the serious hazards of the D & C and D & E procedures are that the application of instruments to the uterine wall may cause a perforation thereof, if excessive force is applied. It is to this problem that this invention is addressed in providing means to reduce the occurrence of perforation caused by sharp or aspirating instruments and/or uterine probes.

The problem is compounded by the fact that the passive step of pushing or probing the surgical instrument or instruments to find a desired position on the uterine wall preparatory to the actual measuring and curettage steps or procedures, requires different properties for the instruments than those of the active or pulling step for accomplishing the curettage.

This invention involves the provision of means for reducing the danger of damaging or rupturing living tissue during a passive, probing or pushing step of a surgical instrument, by means of a structure which may either be an attachment to, or made integral with, said surgical instruments, while being without effect during an active, pulling step.

Accordingly, it is an object of this invention to provide gynecological surgical instruments with force limiting means, effective during a passive, pushing step of a procedure to avoid uterine wall perforation, and ineffective during an active, pulling step of the procedure.

It is another object of this invention to provide a force, limiting attachment to a surgical instrument effective during a passive, pushing step of a procedure, and ineffective during an active, pulling step of the procedure.

Another object of this invention is to produce a surgical instrument or attachment thereto that limits the force applied against an object when the instrument is pushed against said object and is inoperative during a pulling operation that is easy and economical to produce.

Thus, according to the present invention there is now provided in combination with a surgical instrument applied by a pushing action to place said instrument against human tissue, and then, to a pulling action along said tissue, the improvement comprising means for limiting the pushing action of said instrument against said tissue to a predetermined force, said means being inoperative during said pulling action.

The invention also provides an adapter for use with a surgical and aspirating instrument having a handle and an operating end, said adapter comprising a tubular member surrounding said handle, spring means within said tubular member for biasing said handle in a direction toward said operating end, means operative to inhibit rotation of said handle and limit forward movement thereof within said member, said spring biasing acting as a force limiting means for forward motion of said tubular member such that overcoming of said bias allows relative backward movement between said handle and said tubular member only when said tubular member is moved in said forward direction.

The invention further provides a surgical instrument having a handle and an operating end, said instrument comprising a piston connected to said operating end and arranged for movement within said handle, spring mean within said handle for biasing said piston in a forward direction with a predetermined force means cooperating with said piston for preventing rotation thereof, and means for limiting the forward motion of said piston within said handle such that a forward motion of said handle against an object causes forward motion of said operating end unless a predetermined force is exceeded to cause a relative movement between said handle and said operating end.

The invention still further provides an adapter for use with a surgical instrument, comprising a tubular member having a rear end cap, a second tubular member having an open end and a closed end, disposed within the first mentioned tubular member with said closed end closer to said end cap, a compression spring abutting said closed end of said second tubular member and said end cap of said first tubular member, to provide a forward bias to said second tubular member, means preventing relative rotational movement between said members, and a front end closure releaseable connectable to the open end of said inner member, for affixing a surgical instrument of said adapter handle.

The invention provides yet further a adapter for use with an irrigating or aspirating surgical instrument, comprising an outer tubular member and an inner tubular member defining annular confines thereinbetween, said inner tubular member having a front end connectable to a hollow surgical instrument and means connectable to a source of low pressure for effecting a suction action within said member; a bore extending transversely through the wall of said inner member and communicating with the atmosphere, valve means displaceable within said confines selectively blocking and opening said bore, a biasing spring disposed within said confines and abutting between said valve means and an end closure of said adapter, allowing relative axial movement between said members against the biasing force of said spring, and hand manipulatable element for selectively displacing said valve means from blocking said bore against the action of said spring, whereby the suction action within said member is controlled.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 7 and 8 are cross-sectional and exploded views of still a further embodiment;

FIG. 9 is a partly exploded view of a modification of the embodiment of FIG. 8;

FIGS. 10 and 11 are cross-sectional and exploded views of a further embodiment;

FIG. 12 is a cross-sectional view of an in line adapter or a conventional irrigating and/or aspirating curette;

FIG. 13 is an exploded view partly in cross-section of another embodiment of an irrigating and/or aspirating curette and, FIGS. 14 and 15 are cross-sectional and exploded views of a controlled flow irrigating and/or aspirating curette according to the present invention.

Figure 1:
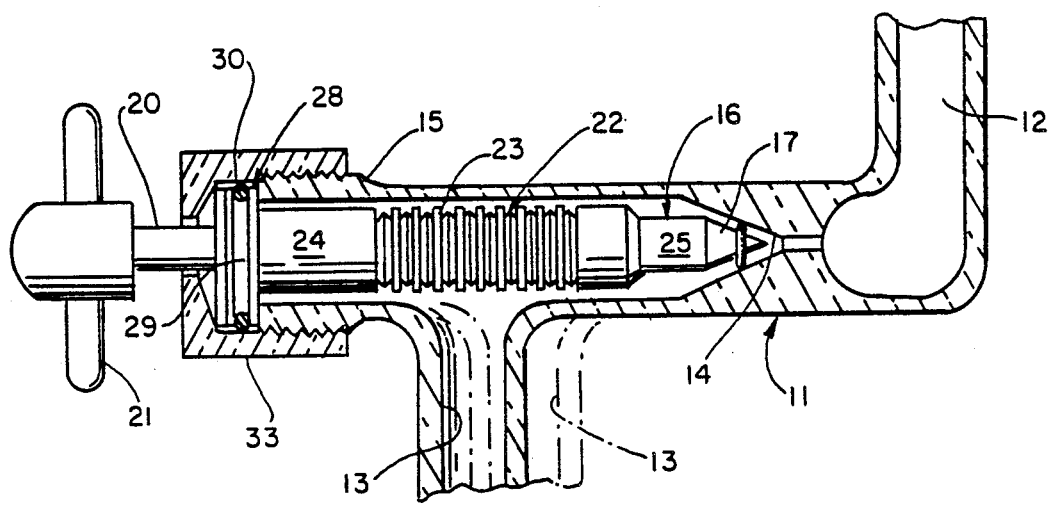
FIGS. 1 and 2 are plan views of a prior art uterine probe and uterine curette, respectively.

There is shown in FIG. 1 a conventional uterine probe 10 comprising a handle 12 to which is fixedly secured a probe shaft 14 with a scale or graduations thereon, usually in centimeters, and which may have a slide indicator 16 frictionally engaged therewith for indicating the measurement. The probe 10 has a rounded end 18 to aid in avoiding the puncturing of the wall of a uterus being measured. The shaft 14. as shown, may be flexible or rigid with a slight curvature close to end 18. Although the end 18 is rounded, the insertion of the probe, such that the end 18 contacts the wall at the upper end of the womb, can still produce a perforation if too much force is utilized.

Figure 2:
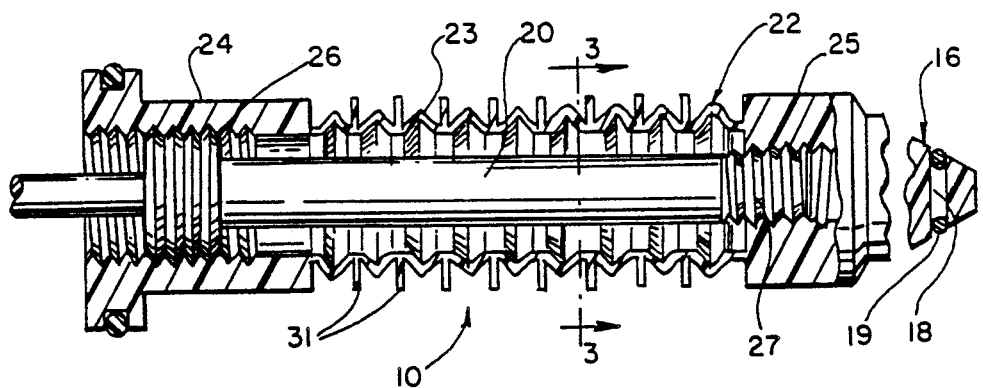

With reference to FIG. 2 there is shown a conventional uterine curette 20, having a handle 22 to which is fixedly connected a shaft 24 with its free end terminating in a conventional curette blade or loop 28. The curette 20 may have a hollow shaft 24 and handle 22 for rendering the device either as an irrigation curette or an aspirating curette. Of course, the handle would have conventional means for connecting the curette to aspiration or irrigation apparatus.

The devices 10 of FIG. 1, or 20 of FIG. 2 are both utilized by insertion of the end 18 o 28 of the instruments through the vaginal opening into the uterus. The instrument is then pushed until it contacts the upper uterine wall, care being taken to avoid pushing the instrument beyond the fundus. The bringing of the instrument to the highest point of the uterus is considered a passive movement in that only a positioning of the instrument is effected, however, the danger exists that too great a pressure will be exerted and uterine wall perforation will result.

With the probe 10 of FIG. 1 reading and/or setting of the slide indicator 16 and withdrawal of the probe would complete the measuring procedure. The instrument of FIG. 2 would, after being placed at the highest point of the uterus, start its normal, active curettage movement of the blade or loop 28 of instrument 20 during a pulling movement in the direction for removal of the instrument form the uterus.

The deficiency of the prior art probe and curettage implements of FIGS. 1 and 2 may be obviated by the structure of the following embodiments, wherein the rigid connection of the handle, grasped by the operator, and the shaft is changed to a sliding one upon the application of a predetermined force during the passive insertion step, and, during curettage or the removal operation of the curette, the shaft resumes and maintains a rigid connection with the operator grasped handle.

Figure 3:
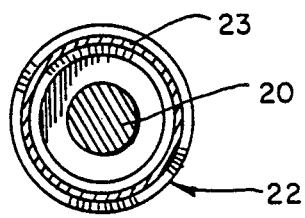
FIG. 3 is an exploded view of a uterine curette embodying the inventive concept of this invention.

The embodiment of FIG. 3 illustrates a uterine curette 30 according to the present invention, having a hollow handle 32 with an externally threaded portion 34 at one end and a internally threaded portion 36 at its other end. An end closure member 38 has a first threaded portion 40 arranged to mate with the internal threaded end 36 of handle 32 and a second threaded portion 42 upon which is an adjustably mounted, internally threaded spring base member 44. A straight open coil, helical, compression spring 46 is arranged to slip over second threaded portion 42 of end closure member 38 with one end abutting against adjustable spring base member 44, the position of which would affect the spring bias. The curette blade or loop 48 is formed at one end of a shaft 50 which has a scale or graduations thereon with a friction slide indicator means 52 mounted thereon to allow the instrument to also be utilized as a uterine measuring probe or for indicating the maximum insertion length to be used for the curettage operation The other end of the shaft is passed through and journaled in the front closure member 54 of the handle 32. Front closure member 54 has an internal thread which mates with the external thread 34 of the handle 32 and also has a hand operated set screw 56 for rigidly securing the shaft 50 to the handle, then desired. A generally cylindrical piston 58 is secured, for example, by a set screw 60 to the other end of shaft 50. A longitudinal groove 62 in the external surface of piston 58, and extending substantially the entire length thereof, is arranged to cooperate with a pin 64 with extends into the interior of handle 32 to inhibit any rotary motion of shaft 50 and its curettage blade or loop 48, and also to act as a stop to prevent the piston from disengagement with said pi 64.

Assembly of the instrument 30 requires, after the selection of the appropriate curette blade or loop 48 with its shaft 50, the sliding of the shaft end opposite the blade or loop through the opening of front closure member 54 and then attaching the piston 58 to said shaft end by means of set screw 60. The piston 58 is inserted into the handle 32 with pin 64 in groove 62, and the front closure member is threaded onto externally threaded portion 34 of the handle 32. End closure member 38, with spring member 46 mounted on second threaded portion 42 and in contact with adjustable spring base 44, is then screwed into the internally threaded end 36 of handle 32 such that the spring 46 abuts the piston 58. With set screw 56 released, force exerted along the longitudinal axis of the instrument 30 in the direction toward curettage blade or loop 48, would allow movement of the handle 32 along shaft 50 in the direction of the applied force when the blade or loop abuts an obstacle and the force applied is greater than the spring force. With set screw 56 tightened the handle and shaft are locked to provide an instrument that would now operate like the prior art instrument of FIG. 2.

It is to be noted, however, that the back sliding motion of the shaft 50 towards the handle 32 may also be attained without spring member 46 by providing means (not shown) to enable the shaft to have several stop points on its way back along the handle 32.

Figure 4:
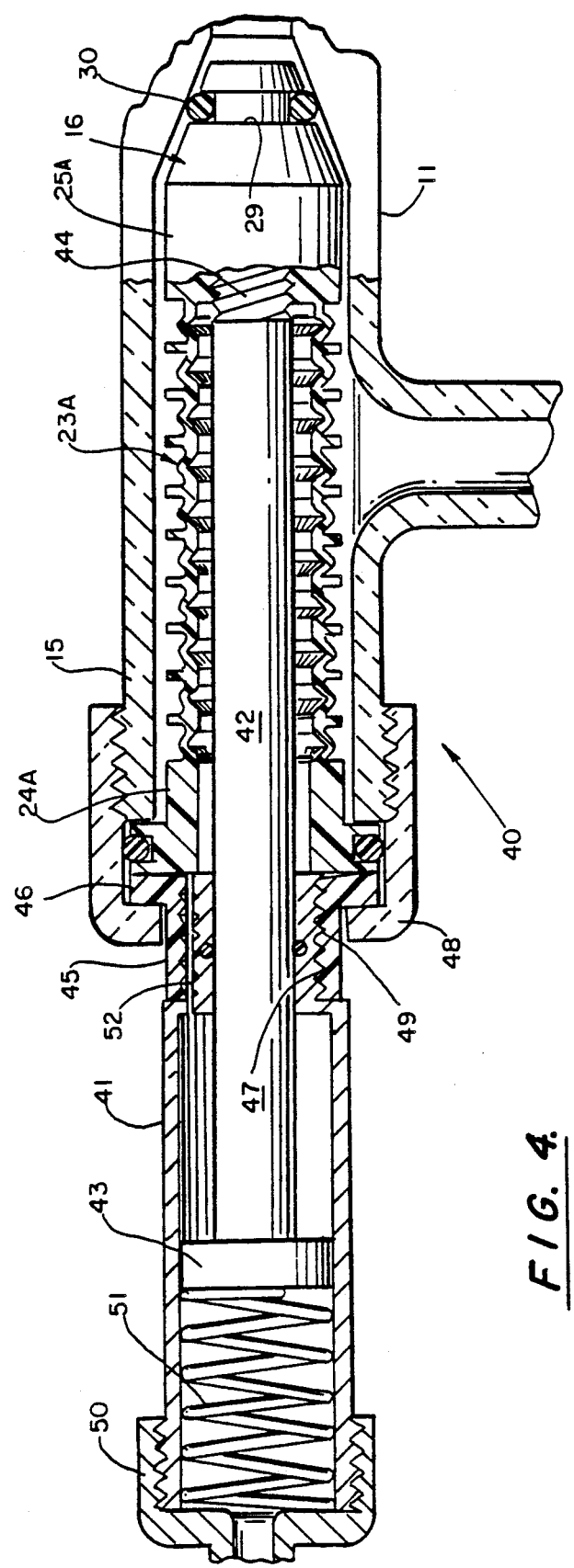
FIG. 4 is a schematic representation of another embodiment of this invention for attachment to a conventional uterine curette containing the structure for the practice of the inventive concept of this invention.

Another arrangement for providing for the passive force limiting feature to a conventional, commercially available curette with aspiration and/or irrigation connections or endoscopic instrument such as hysteroscop) or intrauterine contraceptive device inserter, is shown schematically in FIG. 4. The curette 70 has clamped thereto an offset arrangement 72 which is used as the handle for the assembly. The offset arrangement 72 comprises a clamp 74 which engages the curette in a locked relationship. A bar or rod 76, secured to the clamp 74 and bent to be parallel with the handle of the curette, has attached thereto a handle 32 which contains all of the elements of the like handle of FIG. 3.

Figure 5:
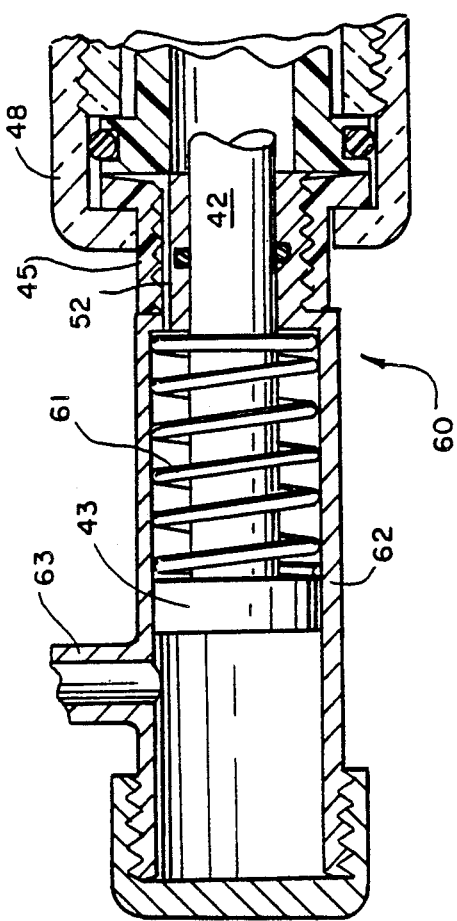
FIG. 5 is a cross-sectional view of a modification of the embodiment of FIG. 3.
Figure 6:
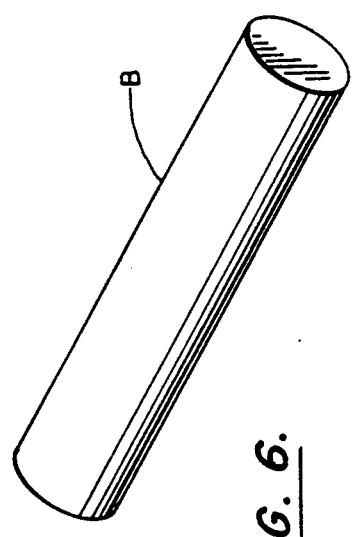
FIG. 6 is an exploded view of the embodiment of FIG. 5.
Figure 1:
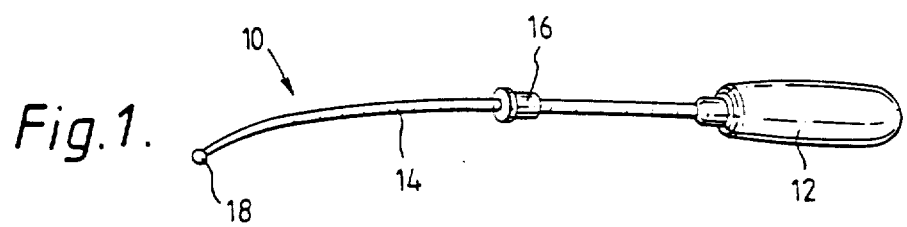
Figure 2:
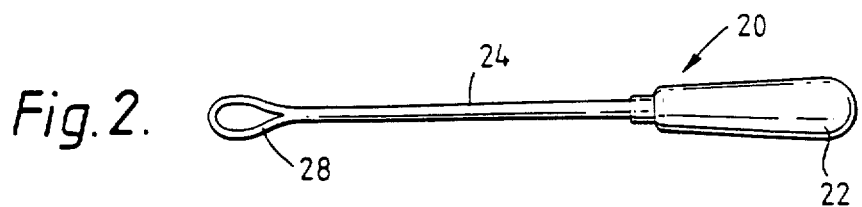
Figure 3:
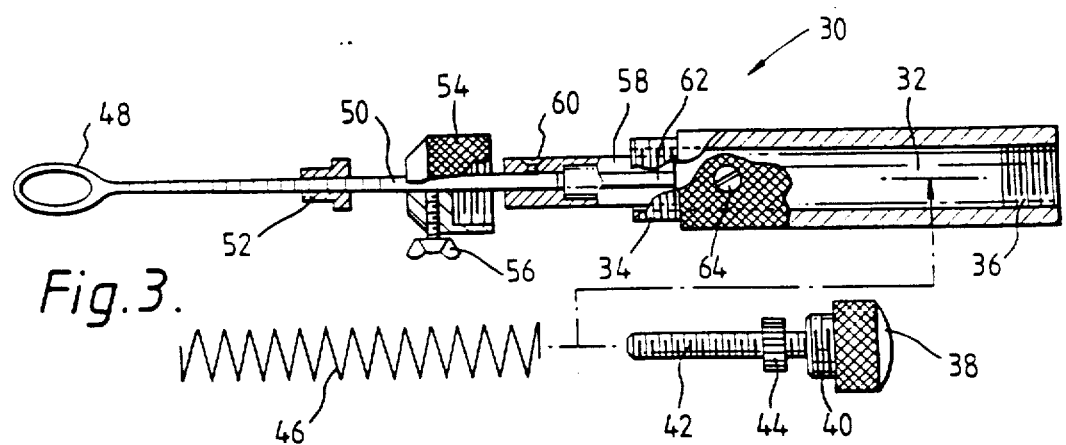
Figure 4:
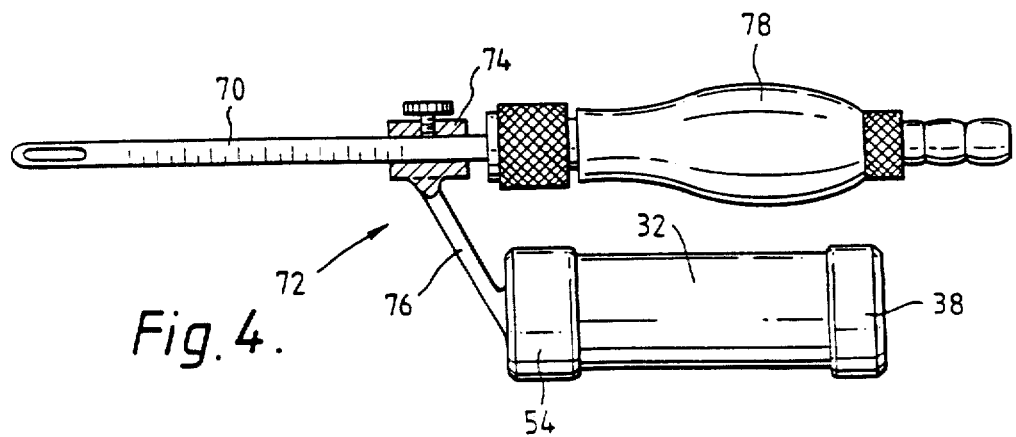

In FIGS. 5 and 6 there is illustrated a modification of the embodiment of FIG. 3. The main differences between this embodiment and the one shown in FIG. 3 reside in the handle member 80 which, as seen is provided with a front end portion 82 of a reduced external diameter and having a meandering slot 84, as well as in the ring 86 rotatably fitting over the portion 82 and in the L-shape projection 88. extending from the front surface of the piston 58. The set screw 56 is provided with an unthreaded extension 90, which, in assembly (see FIG. 5) extends into and is guided by, the slot 84.

With this arrangement it is possible to eliminate the piston's movement inside the handle member 80 by means of the ring 86. When the latter is rotated, e.g., counterclockwise, the screw's extension 90 will engage the projection 88 thereby locking the piston in place. A clockwise rotation of the ring 86, will retrieve the extension 90 from its piston engaging position.

Figure 7:
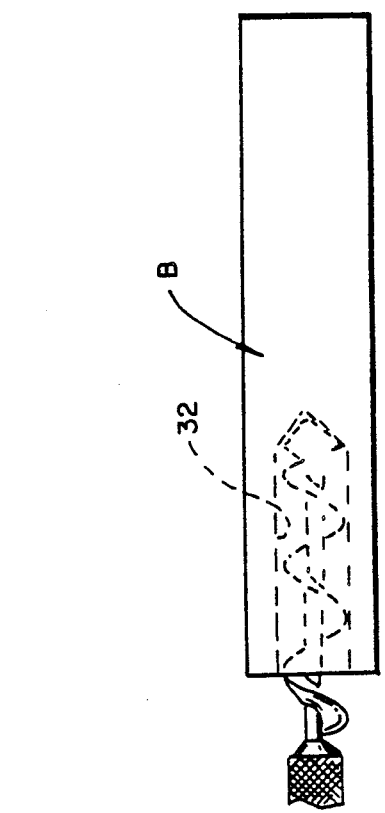

In FIGS. 7 and 8, there is shown an adapter according to the present invention, for converting standard surgical hand instruments into instruments of safer use, as explained hereinbefore. Seen is an outer cylindrical member 92 having an internal recess 94 at its rear end, an inner, closed bottom, tubular member 96 configured to closely fit inside the member 92 and having a projection 98 complementarily configured to fit with clearance inside the recess 94. The rear end of the member 92 internally threaded to be engaged by a threaded closure 100. A biasing spring 102 with its ends abutting against the inner face of the closure 100 and the outer face of the bottom 104 of the member 96, when the adapter is assembled, is also provided. The front end of the inner member 96 is likewise threaded for engaging with a conically shaped, front closure member 106 having a slot 108.

As can advantageously be seen in FIG. 7, a standard surgical instrument 110, having a shank 112 and a handle 114 is engaged by the adapter with the handle 114 first inserted into the member 96, thereafter the closure member 106 is slipped over the base of the shank 112 and finally, the closure is threaded in place, thus securing the instrument inside the adapter. During use, when a force, exceeding the biasing force of the spring 102 is exerted on the shank 112 in an axial direction, the handle 114 will push the member 96 against the spring and slide within the outer member 92, which latter member is held by the user's hand.

While in the embodiments described heretofore, the instrument to be used was inserted inside the adapter, it can readily be understood that an instrument may, alternatively, be affixed at the front end of such an adapter as, e.g., seen in FIG. 9. Hence, instead of the conically shaped closure member 106. There may be provided a closure 116 fitted with flexible clasp means 118, detachably clamping. e.g., an intrauterine contraceptive device introducer 120, or devices such as an hysteroscop.

Referring to FIGS. 10 and 11, there is illustrated an adapter similar to the adapters previously described, however, working with a tension spring instead of a compression spring. The adapter comprises an outer gripping tubular member 122 fitted with a screw 124, an inner tubular member 126 having a guiding slot 128, a tension spring 132 affixed at one end by means of, e.g., an inner screw 130 to the inner surface of the member 126, adjacent one end of the slot 128. The other end of the spring 130 is attached to the screw 124', the end portion of which screw serves also as a guiding element for guiding the axial movement between the members and preventing a rotational movement thereof. The front end of the inner member is fitted, in addition with the conically shaped closure 136 with a slotted collet 138 for providing a better gripping action on the shank 140 of a hand tool inserted therein.

An embodiment of an adapter that can be inserted between an aspirating and/or irrigating curette and its handle is illustrated in FIG. 12. In this embodiment there is provided a curette receiving member 142, into which a conventional curette is received. Member 142 is connected to, or constitutes an end portion of, a tube 144. The tube 144 passes through a handle 146 having apertured end closures 148 and 150. The front end of the tube is fitted with a cylinder 152 opening 158 through which the tube 144 passes. A spring 160 is interposed between the tube 144 and cylinder 152. Another spring 162, of a larger diameter, surrounding the cylinder 152 and the tube 144, abuts the inner surface of the closure 150 and the ring 154.

As can be understood, when the curette manipulated by the handle 146 encounters an obstacle, it is moved backwards against the force of the spring 160 until it is compressed. A further push of the handle forwards will move the cylinder and the compressed spring backwards against the force of the second spring 162.

Avoidance of the provision of O-ring seals for an aspiration system may be achieved by the embodiment of FIG. 13. A conventional fitting 168 which forms an internal part of a handle incorporating the concept of the present invention. The opposite end of fitting 168 has a connector 170 arranged to receive tubing connected with an aspirator pump. The handle is comprised of three pieces, two end caps 172 and 174, each having a hole therethrough for the fitting 168. Both end caps are internally threaded to mate with external threads on internally bored handle body 176. Two flanges appear on fitting 168, one, numbered 178, may be part of the connector 170 and is proportioned to be journaled in the end cap 174, and the other, numbered 180 abuts end cap 172 and is journaled in the bore of handle 176. To assemble the curette, the end cap 172 is first applied to the fitting 168 to abut flange 180. A spring 182 is then applied to abut flange 180 and handle body 176 is screwed to the end cap 172. End cap 174 is applied to the end of handle 176 and forms a base for the spring 182. Thus, when the handle 176 is pushed forwardly at a force greater than that predetermined, and the curette tip bears against the uterine wall, the handle can move forwardly against the action of spring 182. A stop, for example, in the form of a C-ring 184, could be provided adjacent receiver portion 166 to abut the forward side of end cover 172. To avoid rotation between the handle and the interior parts, the provision of a flat portion on the flange 180 for mating with a fixed inset in the bore of the handle 176, would be one of many simple solutions.

Figure 15:
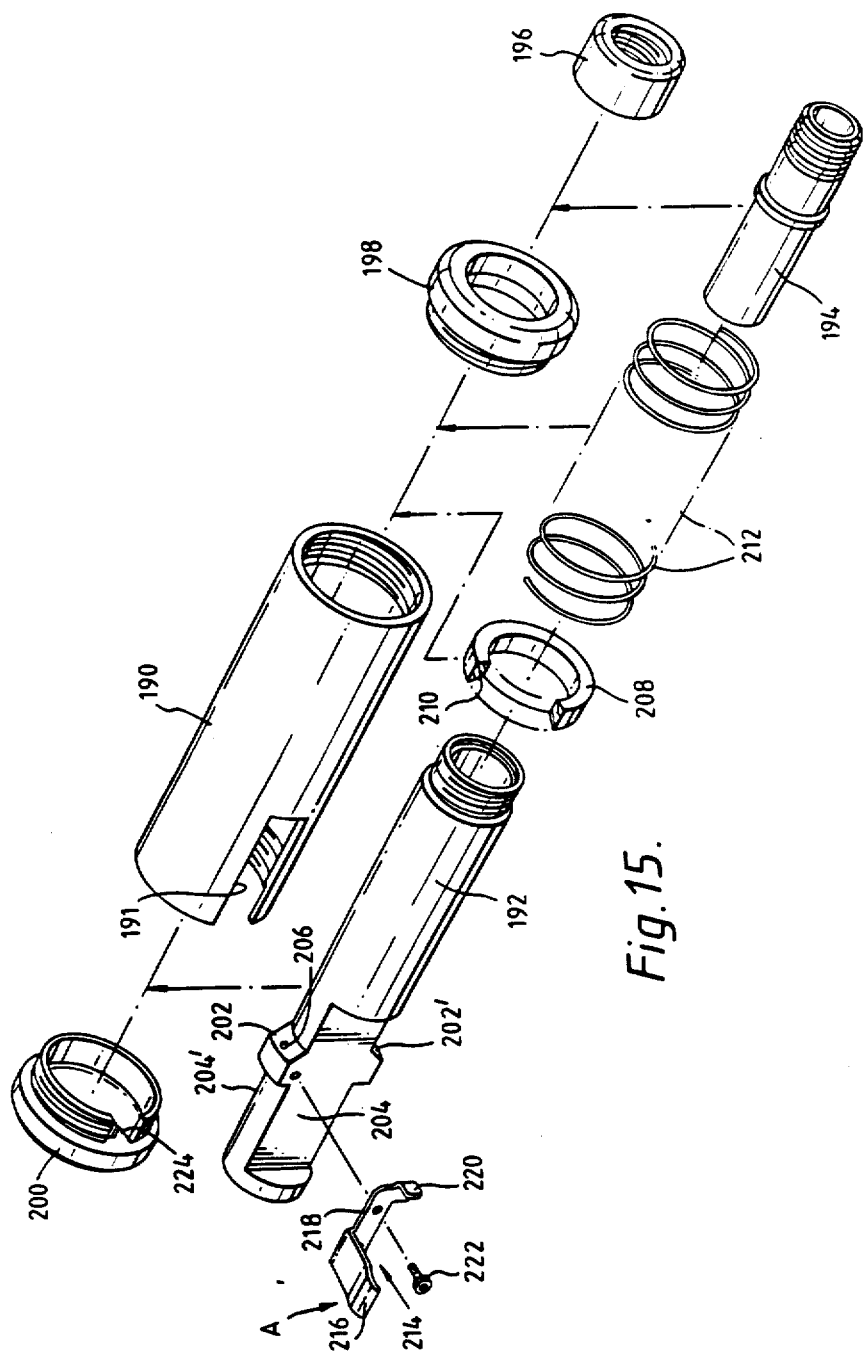

Turning to FIGS. 14 and 15 there is illustrated an adapater for use with an aspirating and/or irrigating curette or the like, consisting of an outer tubular member 190 having a slot 191 in its wall, an inner tubular member 192, a suction fitting 194, a suction fitting nut 196 securing the fitting 194 to the member 192, an end closure 198 and a front closure 200. The member 192 is configured to have two oppositely disposed conical surfaces 202 and 202' and two flat side faces 204 and 204'. A bore 206 leads from the surface 202 into the interior of the member 192. A control ring 208 having a slating surface 210, complementary shaped to the surfaces 202 and 202', is slipped over the member 192 and also serves as an abatement for a spring 212 interposed between the tubular members 190 and 192. The other end of the spring bears against the closure 198. The spring biasing force can be adjusted by the threaded closure 198. Finally, as seen, there is provided air control lever 214 having a manipulatable element 216, an arm, 218 and a tongue 220. The lever 214 is pivotably attached to the flat surface 204 of the member 192 by means of a screw 222.

The operation of this adapter is as follows: Under normal conditions, and as seen in FIG. 14, the spring 212 presses against the ring 208 whereby its surface 210 contacts the conical surface 202 thus closing the bore 206. Fluid will therefore be free to pass, by suction action, from the front end 224 of the adapter to which there is attached, e.g., a commercially available suction currette (not shown), via the interior of the inner tubular member 192 and out through the fitting 194. When it is desired to release the suction action, namely, the negative pressure prevailing inside the inner tubular member, the manipulatable element 216 is pushed in the direction of arrow A causing the tongue 220 to move in the opposite direction due to the lever action about the pivot point of screw 222. In its movement, the tongue acting against the slanting surface 210, displaces the ring 208 in a direction away from the surface 202, thus opening the bore 206 to allow the interior of the member 192 to communicate with the atmosphere.

Hence, as can be understood, as long as the manipulatable element 216 is in its unactuated position the bore 206 remains closed also during the backward movement of the inner member 192, should the curette's tip meet a wall and the forward moving force on the member 190 continuous.

In a semiautomatic mode of operation of this adapter, the manipulatable element 216 is pressed down before the beginning of the use, and held in this position by means of a tooth-like projection 224 made in the front closure 200. Thus no suction action will occur as long as the bore 206 is open. When the suction curette tip reaches a wall during a forward movement of the adapter, the inner member 192 will move backwards, thereby releasing the element 216 from the projection 224, the mating surfaces 202 and 210 will make contact, the bore will close and a suction action will immediately commence. A further forward movement of the adapter by the user will be absorbed by the spring 212 and result in a further backward movement of the member 192 thus preventing any damage to a patient's body by the application of excessive force.

It will be evident to those skilled in the art that, the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

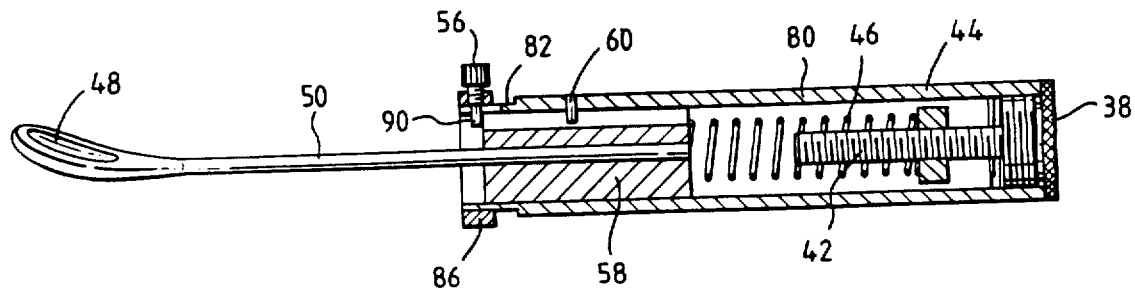

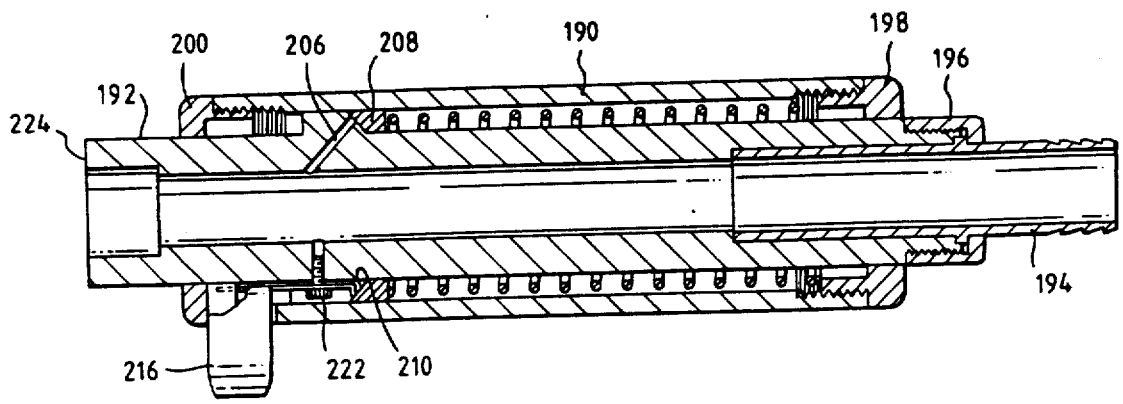

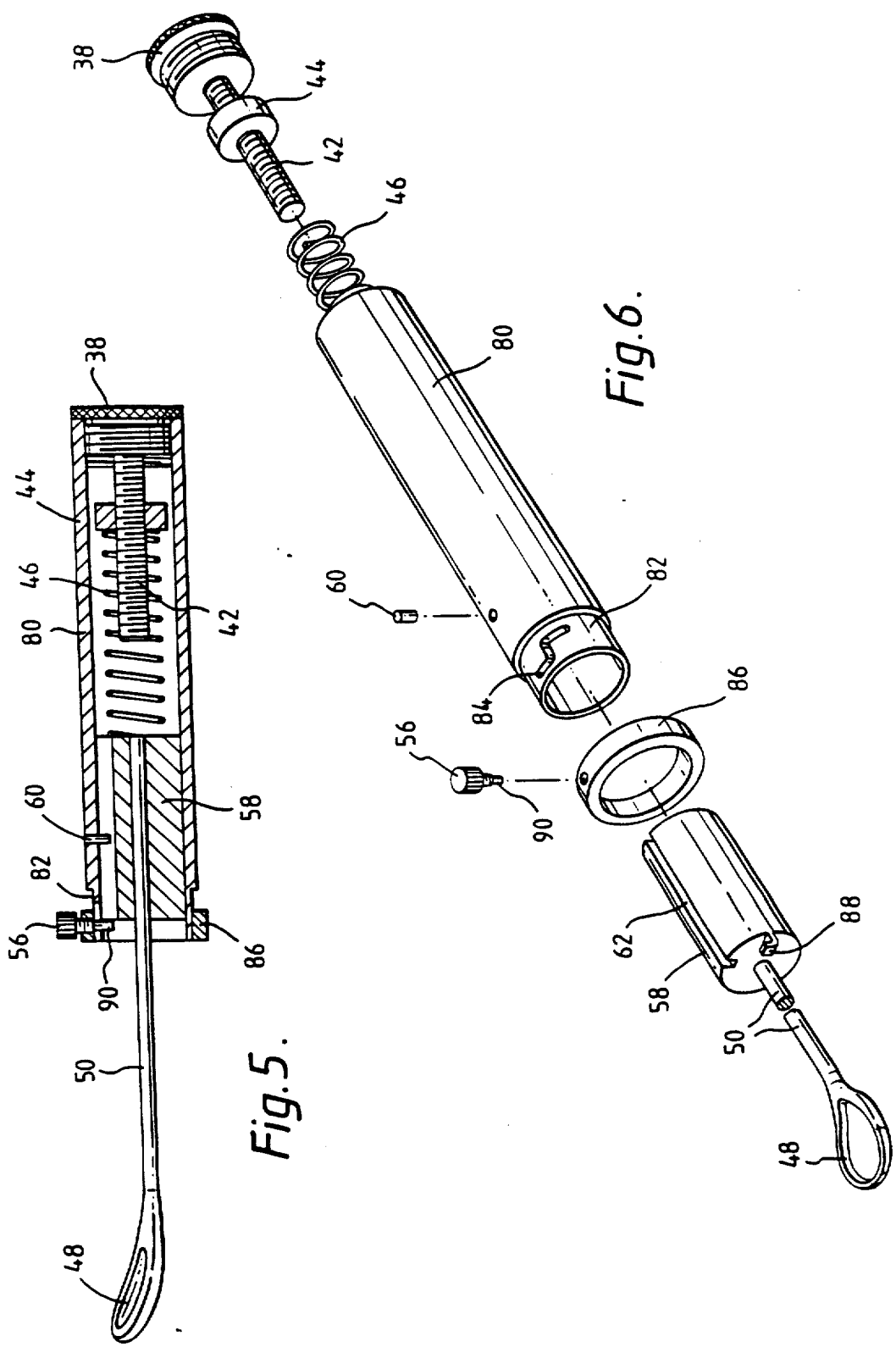

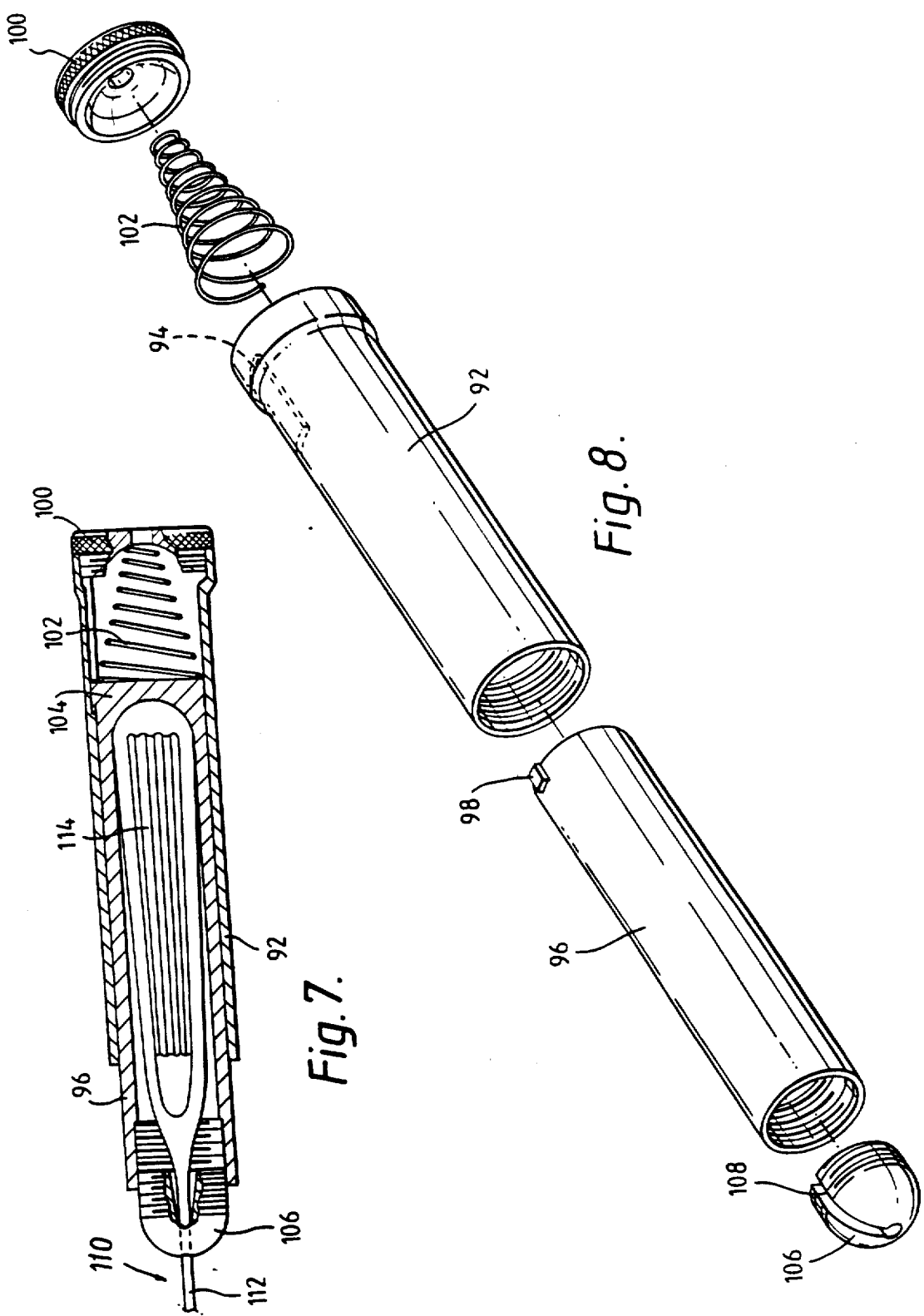

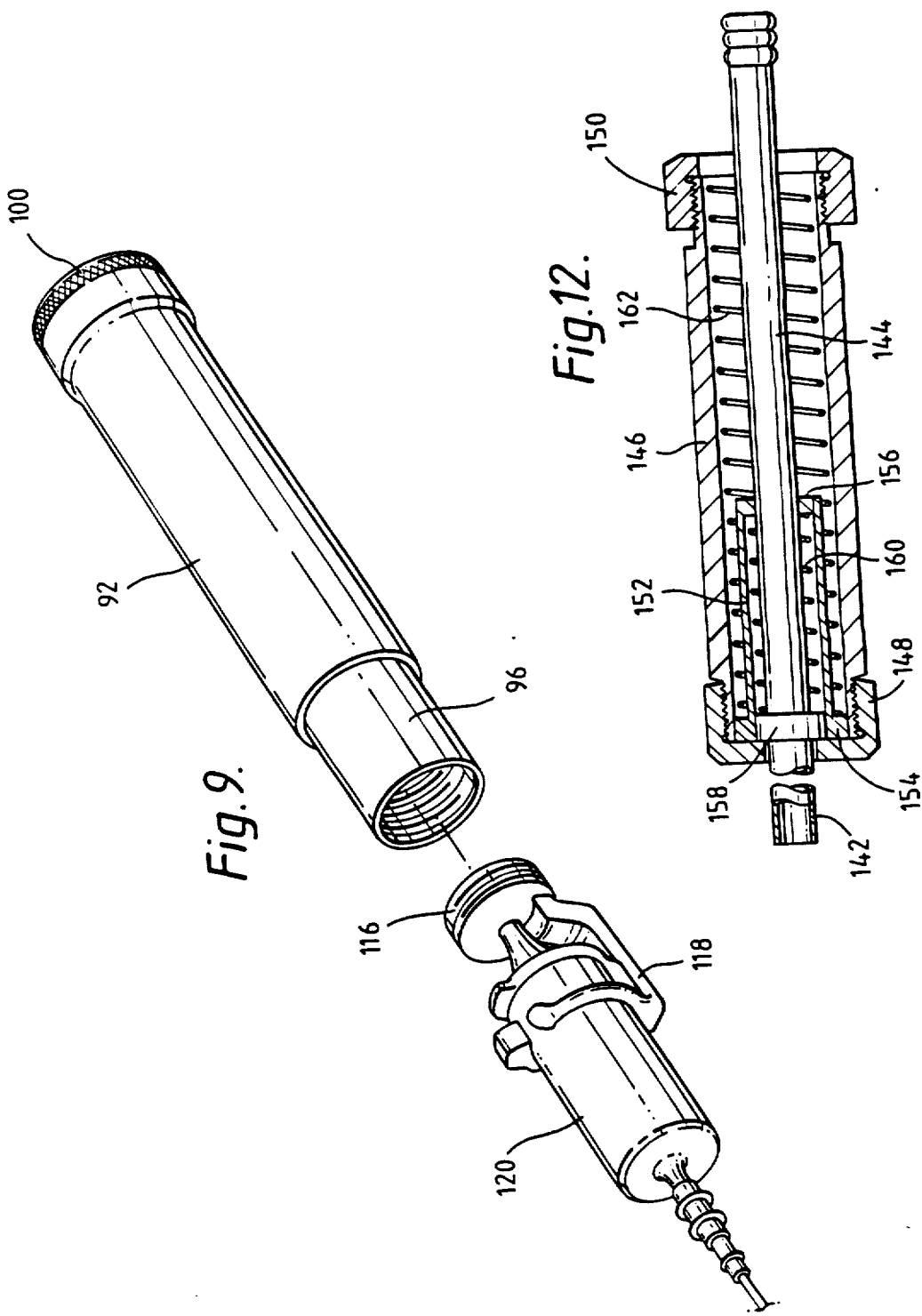

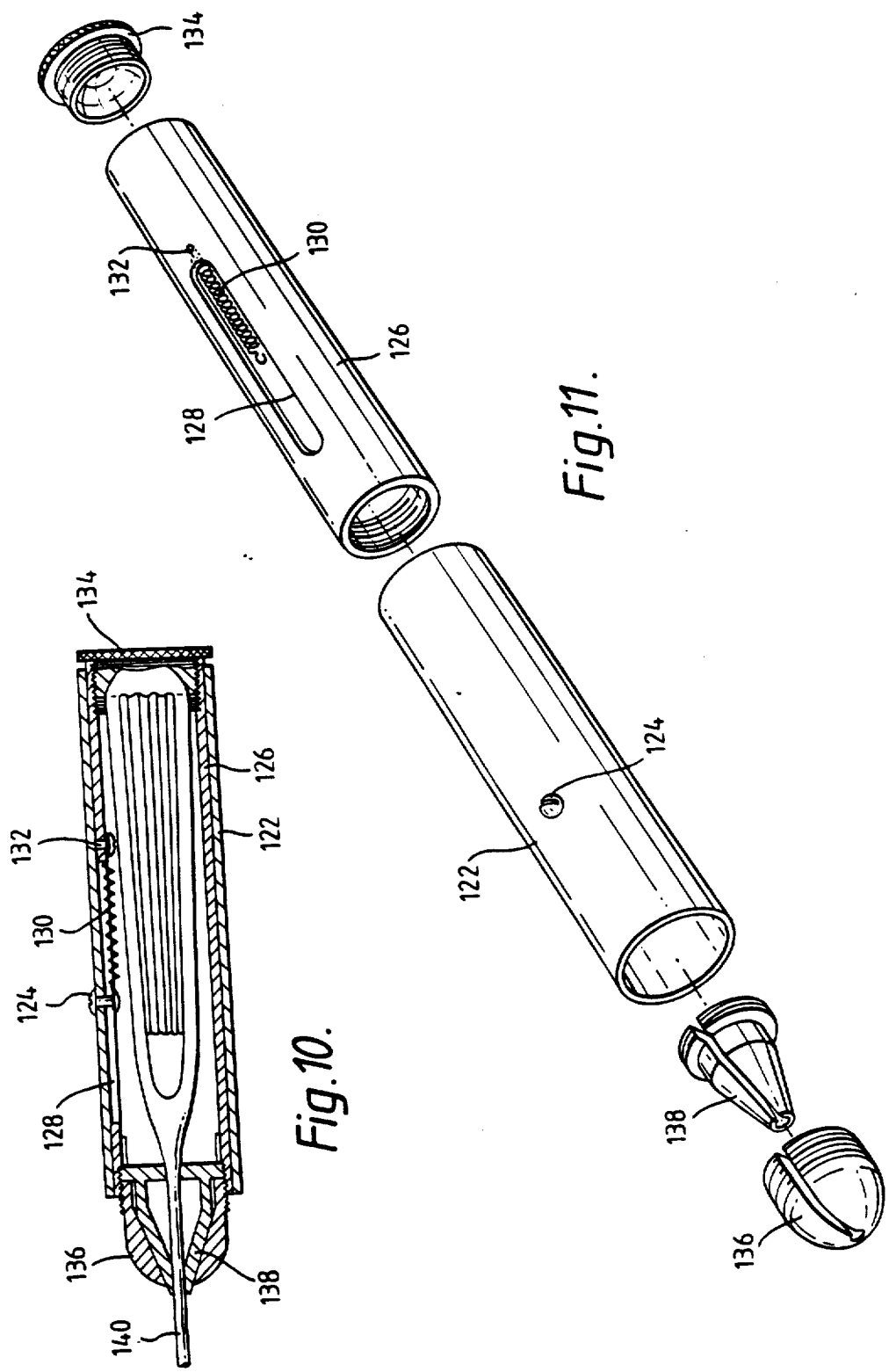

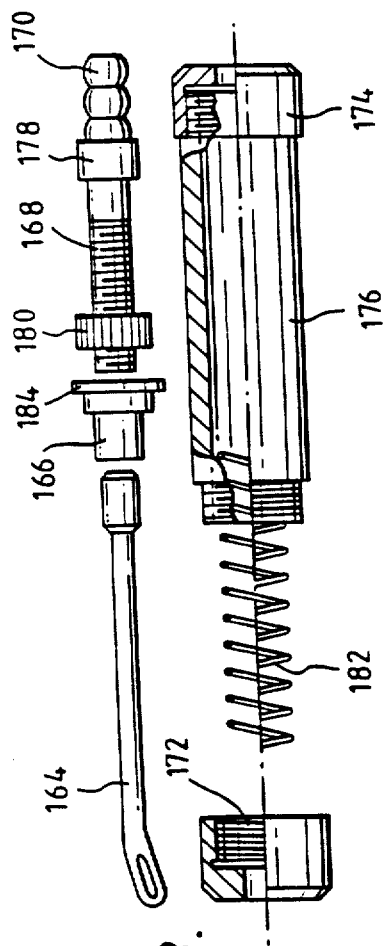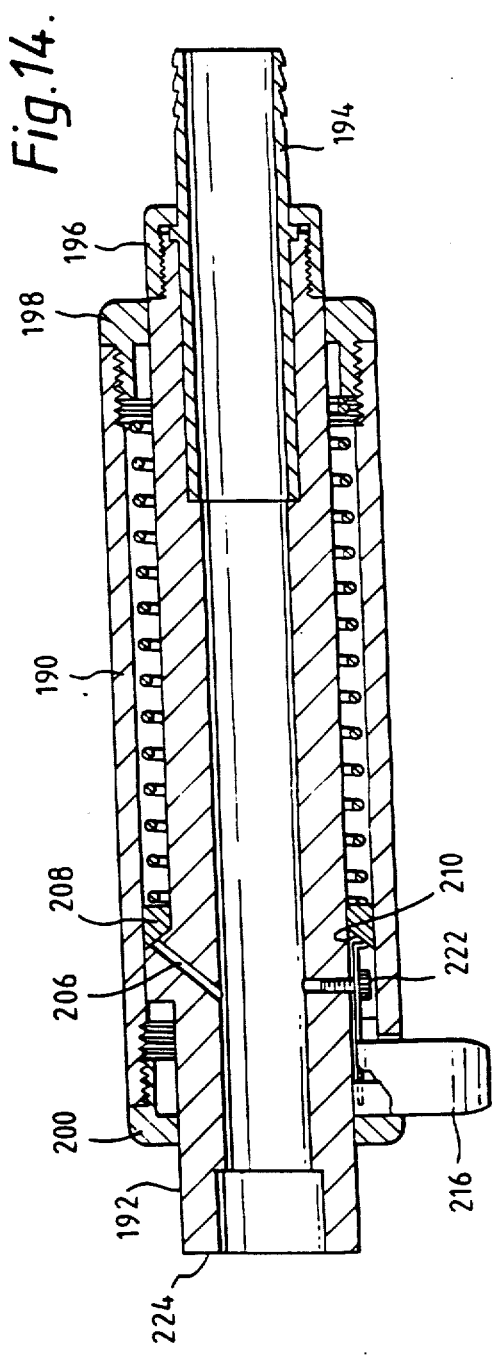

What is claimed is:

1. An adapter for use with a surgical and aspirating instrument said instrument having a handle and an operating end, said adapter comprising:
   a tubular member surrounding said handle;
   spring means within said tubular member for biasing said handle in a direction toward said operating end;
   means operative to inhibit rotation of said handle and limit forward movement thereof within said member,
   said spring biasing acting as a force limiting means for forward motion of said tubular member such that overcoming of said bias allows relative backward movement between said handle and said tubular member only when said tubular member is moved in said forward direction.

2. A surgical instrument having a handle and an operating end, said instrument comprising:
   a piston connected to said operating end and arranged for movement within said handle;
   spring means within said handle for biasing said piston in a forward direction with a predetermined force;
   means for adjusting the biasing force of said spring;
   means cooperating with said piston for preventing rotation thereof; and
   means for limiting the forward motion of said piston such that a forward motion of said handle against an obstacle causes forward motion of said operating end unless a predetermined force is exceeded to cause a relative movement between said handle and said operating end.

3. The surgical instrument as defined in claim 2 wherein said handle is offset alongside the axis of said operating end.

4. An adapter for use with a surgical instrument, comprising:
   a tubular member having a rear end cap;
   a second tubular member having an open end and a closed end, disposed within the first mentioned tubular member with said closed end proximate said end cap;
   a compression spring abutting said closed end of said second tubular member and said end cap of said first tubular member, to provide a forward bias to said second tubular member;
   means preventing relative rotational movement between said members, and
   a front end closure releaseably connectable to the open end of said inner member, said front enclosure having means for affixing a surgical instrument thereto.

5. The adapter as claimed in claim 4 wherein said front end closure is provided with a throughgoing slot, through which slot a shank of a surgical instrument can pass.

6. An adapter for use with an irrigating or aspirating surgical instrument, comprising:

an outer tubular member and an inner tubular member having an annular space thereinbetween communicating with the atmosphere;

said inner tubular member having a front end connectable to a hollow surgical instrument and means connectable to a source of low pressure for effecting a suction action within said member;

a bore extending transversely through the wall of aid inner member and communicating with said annular space;

valve means displaceable within said confines selectively blocking and opening said bore;

a biasing spring disposed within said annular space and abutting against said valve means allowing relative axial movement of said valve means with respect to said bore and hand manipulatable element for selectively displacing said valve means from blocking said bore against the action of said spring, whereby the suction action within said member is controlled.

7. The adapter as claimed in claim 6 further including means for adjusting the biasing force of said spring.

8. A surgical instrument comprising an operating end;

a handle offet along the axis of said operating end;

a piston connected to said operating end and arranged for movement within said handle;

spring means within said handle for biasing said piston in a forward direction with a predetermined force;

means cooperating with said piston for preventing rotation thereof; and means for limiting the forward motion of said piston such that a forward motion of said handle against an obstacle causes forward motion of said operating end unless a predetermined force is exceeded to cause a relative movement between said handle and said operating end.

* * * * *

UNITED STATES PATENT AND TRADEMARK OFFICE
CERTIFICATE OF CORRECTION

PATENT NO. : 5,000,191

DATED : Mar. 19, 1991

INVENTOR(S) : Serge Reiss, et al.

It is certified that error appears in the above-identified patent and that said Letters Patent is hereby corrected as shown below:

The title page, showing the illustrative figure, should be deleted and substitute therefor the attached title page.

Drawing Sheets 1-4, should be deleted and substitute therefor the attached Drawing Sheets, consisting of Figs. 1-15.

Signed and Sealed this

Seventh Day of June, 1994

Attest:

BRUCE LEHMAN

Attesting Officer     Commissioner of Patents and Trademarks

United States Patent [19]

Reiss et al.

[11] Patent Number: 5,000,191
[45] Date of Patent: Mar. 19, 1991

[54] FORCE-LIMITING ADAPTER FOR SURGICAL INSTRUMENTS

[76] Inventors: Serge Reiss, 13/2 Weizman Street, Nahariya, Israel; Joseph M. Brandes, 4 Kiryat Sefer Street, Haifa, Israel, 34676

[21] Appl. No.: 216,924
[22] Filed: Jul. 8, 1988

[30] Foreign Application Priority Data
Jul. 13, 1987 [IL] Israel ......................... 83174

[51] Int. Cl.⁵ ........................................ A61B 10/00
[52] U.S. Cl. .................................. 128/757; 606/119; 606/160; 604/902
[58] Field of Search ............... 128/304, 303 R, 307, 128/311, 314, 315, 341, 357, 361, 749, 757, 758, 774, 778; 604/119, 902, 22; 606/119, 160

[56] References Cited
U.S. PATENT DOCUMENTS

| | | | |
|---|---|---|---|
| 55,620 | 6/1866 | Capewell | 128/314 |
| 3,394,699 | 7/1968 | Koett | 128/311 |
| 3,702,115 | 11/1972 | Elcaness | 128/276 |
| 4,178,810 | 12/1979 | Takahashi | 74/501 R |
| 4,462,405 | 7/1984 | Ehrlich | 128/329 R |
| 4,842,578 | 6/1989 | Johnson et al. | 604/22 |

Primary Examiner—C. Fred Rosenbaum
Assistant Examiner—Adam J. Cermak
Attorney, Agent, or Firm—Schweitzer, Cornman & Gross

[57] ABSTRACT

In combination with a surgical hand instrument applied by a pushing action to place the instrument against human tissue, followed by a pulling action along the tissue, the improvement consisting of an adapter apparatus to limit the pushing action of the instrument against the tissue to a predetermined force, the adapter being inoperative during the pulling action of the instrument. The adapter may advantageously include a biasing spring, which may be adjustable to set the level of the maximum force to be applied.

8 Claims, 7 Drawing Sheets